United States Patent [19]
Brickley

[11] Patent Number: 5,902,552
[45] Date of Patent: *May 11, 1999

[54] ULTRAVIOLET AIR STERILIZATION DEVICE

[76] Inventor: James Lawrence Brickley, 100 Ward Rd., Anaconda, Mont. 59711

[21] Appl. No.: 09/024,698

[22] Filed: Feb. 17, 1998

Related U.S. Application Data

[XX .
[60] Provisional application No. 60/071,100, Jan. 9, 1998.
[51] Int. Cl.$^6$ ........................................................ A62B 7/08
[52] U.S. Cl. ................. 422/121; 250/455.11; 250/522.1; 362/267; 422/120
[58] Field of Search ..................................... 422/120, 121, 422/4; 250/455.11, 504 R, 522.1; 313/318.01, 318.08; 362/267

[56] References Cited

U.S. PATENT DOCUMENTS

| | | | |
|---|---|---|---|
| 4,227,446 | 10/1980 | Sone et al. | 422/121 |
| 4,293,847 | 10/1981 | McCarty | 362/267 X |
| 5,060,121 | 10/1991 | Cunningham et al. | 362/267 X |
| 5,185,015 | 2/1993 | Searle | 55/102 |
| 5,523,057 | 6/1996 | Mazzilli | 422/121 |
| 5,558,158 | 9/1996 | Elmore | 165/122 |
| 5,635,133 | 6/1997 | Glazman | 422/24 |
| 5,656,242 | 8/1997 | Morrow et al. | 422/121 |

*Primary Examiner*—Krisanne Thornton
*Attorney, Agent, or Firm*—Fields and Johnson, P.C.

[57] ABSTRACT

An ultraviolet air sterilization device includes a housing and one or more mounts which connect to germicidal lamp units which protrude into the air stream of an air handling duct. Each lamp has an integral receptacle with an electrical connection for attachment to a source of power from within the housing. The receptacle/lamp combination provides stiffening reinforcement to the lamp. The receptacles connect to their corresponding mounts by means of a threaded connection which enables the lamp units to be easily removed from within the air handling duct.

16 Claims, 4 Drawing Sheets

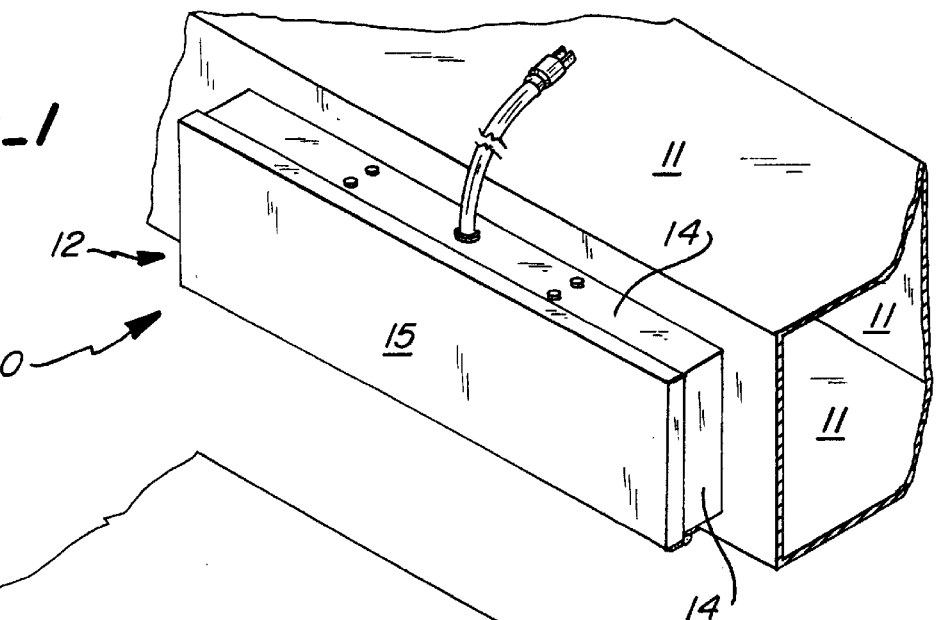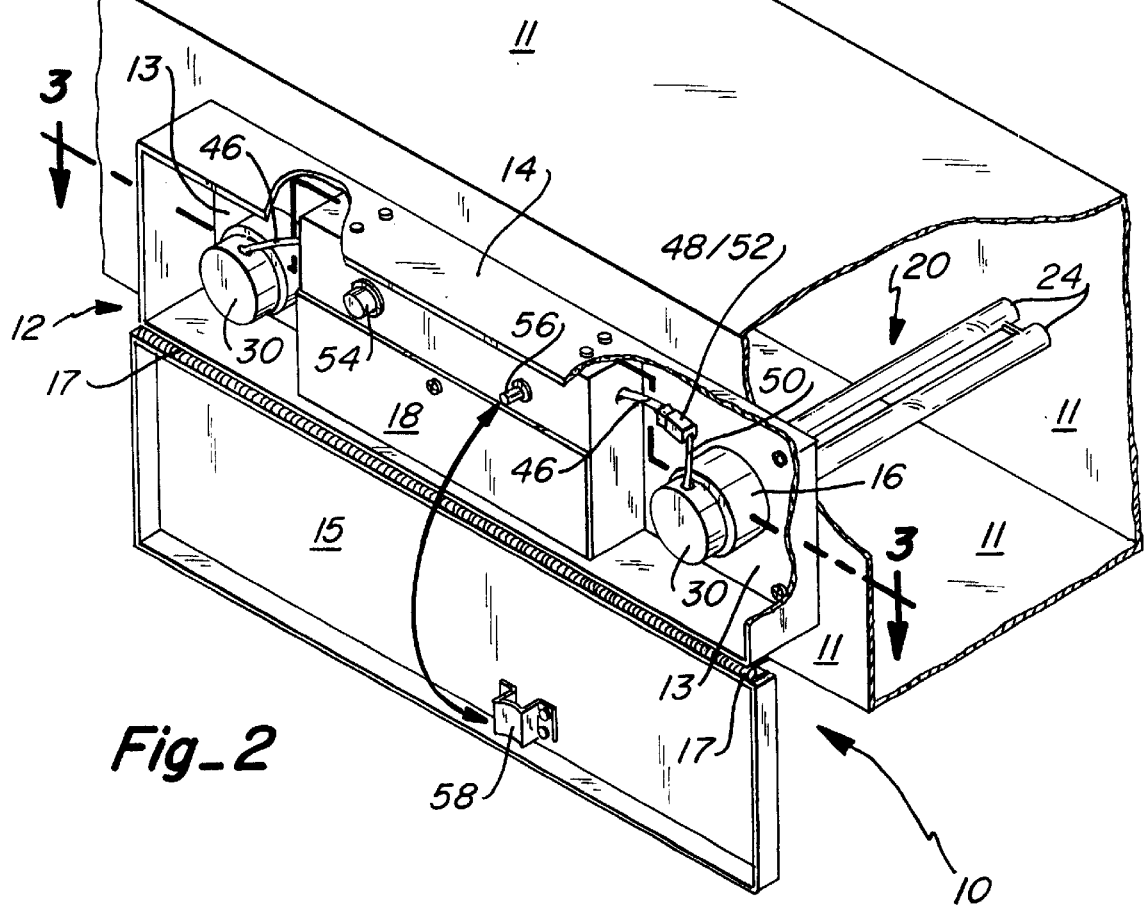

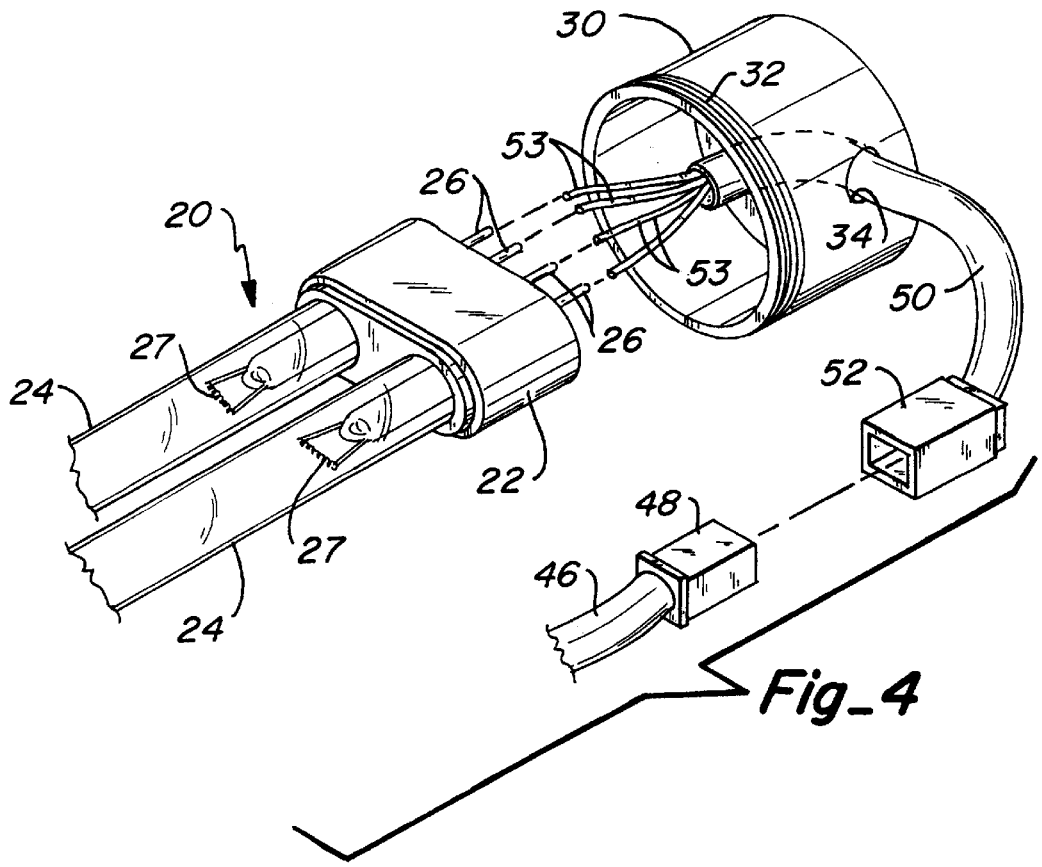
Fig_4
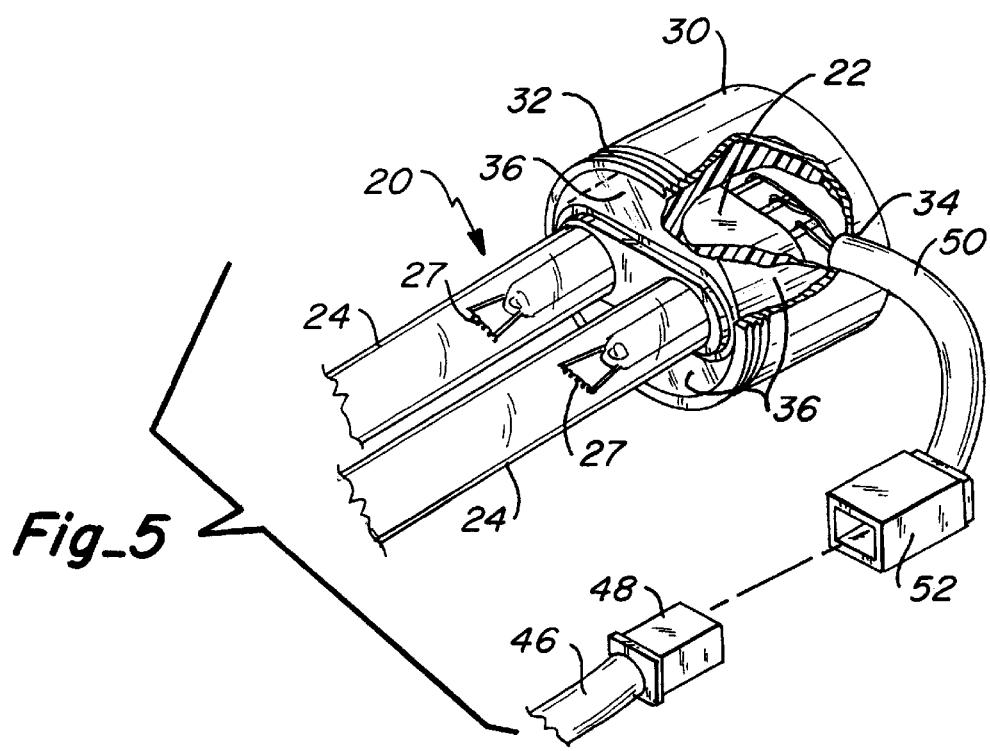
Fig_5

ULTRAVIOLET AIR STERILIZATION DEVICE

This application claims the benefit of U.S. provisional application No. 60/071,100 filed Jan. 9, 1998.

TECHNICAL FIELD

This invention relates to an improvement in an ultraviolet air sterilization device and, more particularly, to an improved air sterilization device which incorporates easily removable germicidal lamps of reinforced construction to withstand the high air velocities present in air handling units.

BACKGROUND ART

The use of an ultraviolet light source to kill bacteria and other microorganisms found in the air has been known for many years. In short, ultraviolet light is of a frequency which is able to effectively kill many types of microorganisms including bacteria and viruses. It is known to place ultraviolet light sources in an air stream in order to assist in the cleaning or sterilization of air introduced into a defined area. For example, it is known to place germicidal or ultraviolet lamps into the air stream of air handling units in order to clean and disinfect air which may be recirculated in an enclosed space. This cleaning or sterilization effect helps in reducing the contraction of bacterial or viral infections in closed air spaces such as offices which may not receive enough quantities of fresh air. Particularly in the winter months for colder climate areas, the introduction of fresh air into air handling units is greatly reduced in such colder months. Therefore, to alleviate the undue recirculation of contaminated air which may contain bacterial or viral agents, a complex set of filters along with ultraviolet lamps may be used.

One major problem with prior art devices which introduce a germicidal lamp directly into the air stream of an air handling unit is that the lamp receptacles which receive the lamps are not strong enough to withstand the continual bending stress created by high velocity air passing over the germicidal lamps. Accordingly, the bases of the lamps fracture or are otherwise damaged by the high velocity. The lamp receptacles themselves may also become damaged due to the continual stress. Over a period of time, the entire air sterilization device may need to be replaced because the lamp receptacles have been so damaged that they are no longer able to hold germicidal lamps.

Additionally, the high amount of dust and other particulate matter which passes through an air handling unit ultimately introduces these particles in the small gaps between the lamp receptacles and the base portions of the lamps. Because the lamps are not effectively sealed with respect to the lamp receptacles, the lamps often cannot be unscrewed from the receptacles which requires the entire sterilization device to be removed from the air handling unit.

Finally, germicidal lamps, like all bulbs or lamps, need replacement over time as they burn out. Germicidal lamps particularly need to be cleaned periodically to remove dust and particulate buildup which form on the lamps. If such buildup is not removed, the ability of the ultraviolet light to penetrate the oncoming air stream is greatly diminished. However, most prior art devices require one to access the air handling unit interior in order to remove the lamps which makes bulb cleaning and replacement difficult.

SUMMARY OF THE INVENTION

In accordance with the present invention, an ultraviolet air sterilization device is provided. In its simplest form, the device includes a housing which contains at least one lamp mount for receiving a germicidal lamp. Each lamp is reinforced in its construction by use of an integral lamp receptacle which is permanently bonded to the base portion of the corresponding lamp. Thus, each lamp and its receptacle form a single unit. The receptacle/lamp unit is easily removed from the housing by mounting it on a threaded connection with respect to a corresponding lamp mount. The base portion of each lamp is sealed with respect to its receptacle by means of a resin or other material.

A hole is cut in the air handling unit to allow the germicidal lamp to be placed in the air stream. The lamp mounts are preferably made of standard threaded conduit mounting flanges. The receptacles are made of a high strength plastic which is able to withstand high temperatures and bending stresses. The lamp mounts are positioned within the housing so that the lamps are the only portions of the device which protrude into the air flow. The use of the conduit mounting flanges and receptacles which are sealed with respect to the lamps greatly reinforce the lamps and their capability to withstand continuous stress. The receptacles are connected to a source of power by means of a quick connect/disconnect. If it is desired to clean or replace a germicidal lamp, an operator simply opens an access panel on the housing which allows access to the receptacle, disconnects the quick connect/disconnect, unscrews the receptacle from its threaded connection with the mount, and removes the lamp. Accordingly, there is no need to independently access the interior of the air handling unit to clean or replace the lamps.

In the preferred embodiment, there are two lamp mounts provided for mounting corresponding germicidal lamps to be placed into the air stream of an air handling unit. Each of the receptacle units has its own quick connect/disconnect connections.

The access panel or lid of the housing may include an interlock switch which shuts off power to the germicidal lamps when the access panel is open. A single rapid start ballast may be electrically connected to the receptacles in order to provide steady current to the germicidal lamps.

By use of the foregoing, germicidal lamps may be easily introduced into an air stream in a reinforced manner because of the construction of the receptacles which are rigidly attached to their corresponding lamps. Because the receptacles themselves are threadably mounted within the housing, the receptacle/lamp units may be easily removed for replacement or cleaning. The receptacle/lamp unit can be supplied as a replacement part wherein the base of the lamps are already sealed to the receptacle with the desired resin material. Each of these units would also include the quick connect/disconnect connection in order that the units can be connected to the existing wiring in the housing.

Each of the foregoing advantages of this invention are achieved with a relatively simple structure which may be manufactured and installed at a minimum cost.

Additional advantages of this invention will become apparent from the description which follows, taken in conjunction with the accompanying drawings.

BRIEF DESCRIPTION OF THE DRAWINGS

FIG. 1 is a perspective view of the ultraviolet air sterilization device of this invention as mounted to an air duct incorporated within an air handling unit;

FIG. 2 is a fragmentary perspective view of the air sterilization device of this invention illustrating the lid or access panel open exposing the interior of the housing, and further illustrating one of the germicidal lamps as it is positioned within the duct;

FIG. 4 is an exploded perspective view of a germicidal lamp prior to mounting within a corresponding receptacle;

FIG. 5 is a fragmentary perspective view of a germicidal lamp mounted within a corresponding receptacle wherein resin or other sealing material rigidly holds the lamp within the receptacle.

BEST MODE FOR CARRYING OUT THE INVENTION

Figure 3:
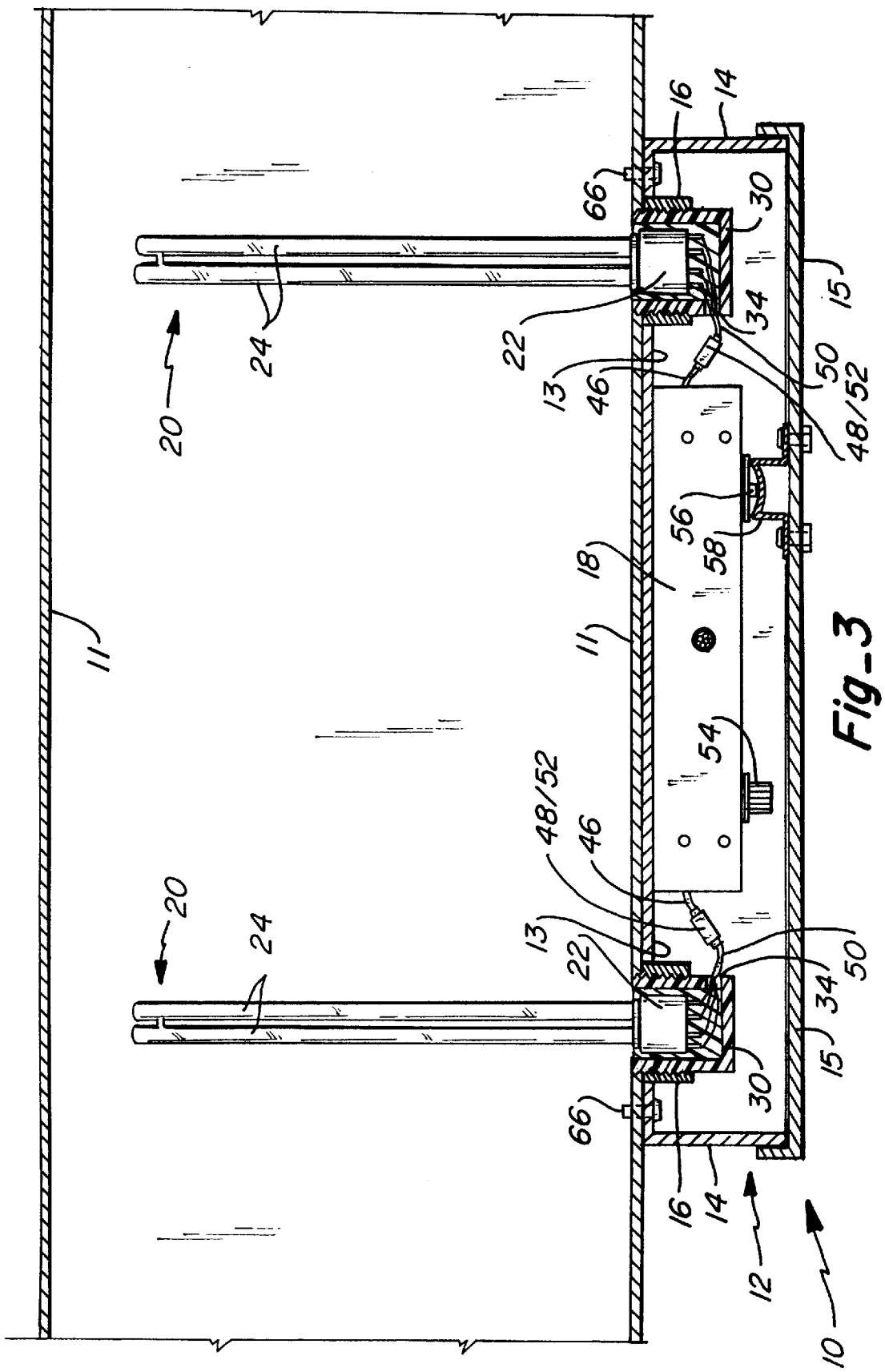
FIG. 3 is a horizontal section, taken along line 3—3 of FIG. 2 illustrating the placement of the germicidal lamps within the air duct and further illustrating the reinforced construction of the receptacle/lamp units as such units are mounted within their corresponding mounts.

FIG. 1 illustrates the ultraviolet air sterilization device 10 of this invention as mounted to the duct 11 of an air handling unit. The sterilization device 10 comprises a housing unit 12 characterized by a box-like structure having side panels 14, a lid or access panel 15, and as shown in FIG. 2, a rear panel 13 which mounts flush to the duct 11. As shown in FIG. 2, the lid or access panel 15 may simply be mounted about hinge 17. A pair of mounts 16 in the form of conduit mounting flanges are positioned at opposite ends of the housing 12 for receiving corresponding receptacles 30, as further explained below. A ballast and circuitry cover 18 may be provided within housing 12 for isolating the ballast (not shown) and the wiring which is used to provide power to the germicidal lamps 20.

As shown in FIGS. 4 and 5, the germicidal lamps 20 each include a lamp base 22 and a lighting element 24 which is illuminated when provided with an electrical power source. A plurality of pin connections 26 transfer electrical power to the lamp filaments 27 housed within the lighting elements 24. Each of the germicidal lamps 20 are mounted in corresponding receptacles 30. Receptacles 30 may be constructed of a UL approved plastic material with external threads 32 which enable the receptacles to be threadably mounted to the mounts 16. The mounts 16 may be constructed of standard 2" electrical conduit with an internal threaded end to receive a corresponding receptacle 30.

Referring to FIGS. 4 and 5, each receptacle 30 has an opening 34 for receiving a transfer cable 50 which comprises a plurality of wires 53 which are connected to pins or terminals 26 on base 22 as by a soldered connection. As shown in FIG. 5, the lamp base 22 is secured within its receptacle by means of a casting resin 36. Resin 36 fills the opening in receptacle 30 and is flush with the interface between base 22 and element 24.

Figure 6:
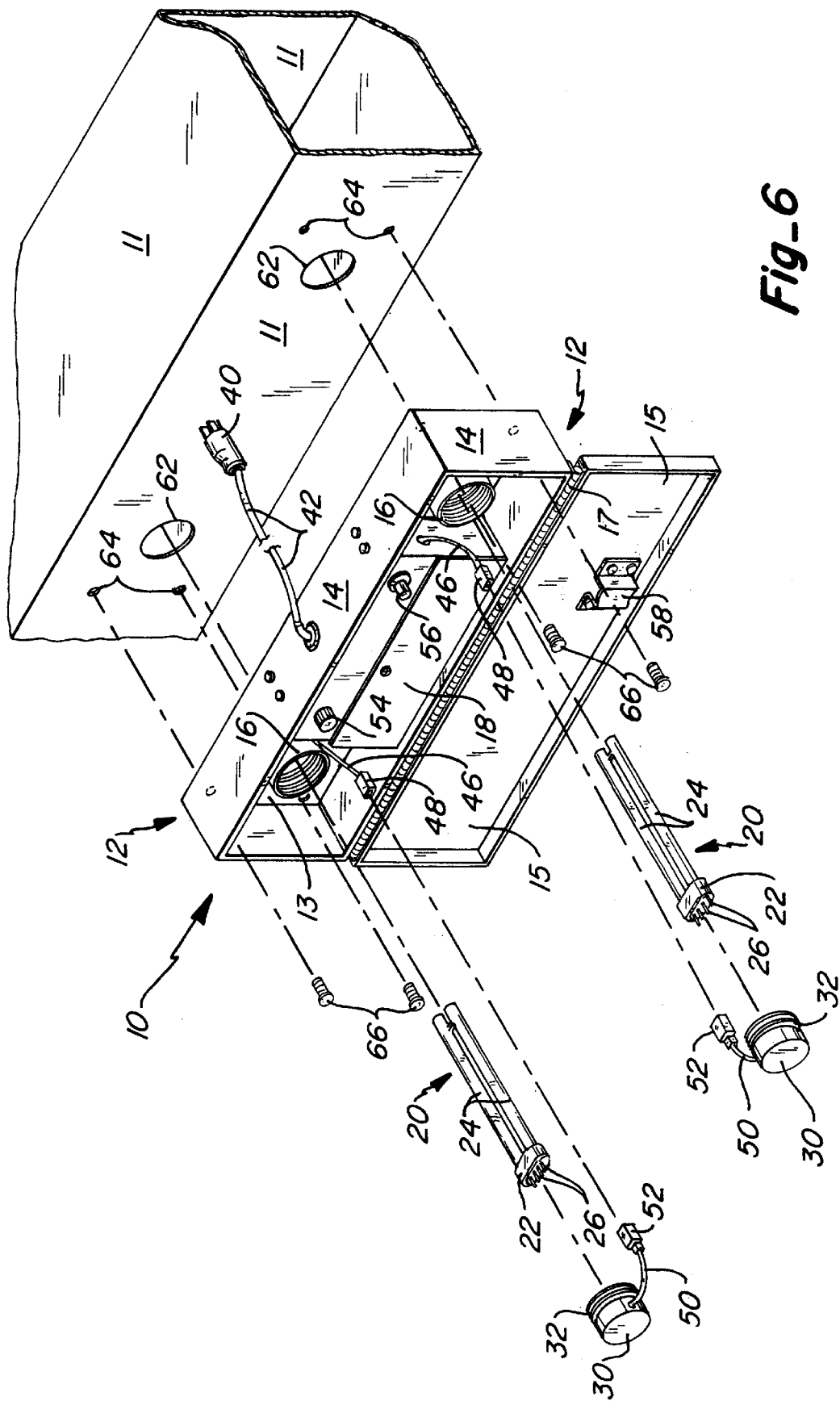
FIG. 6 is an exploded perspective view of the air sterilization device of this invention illustrating further structural details of the component parts.

Referring to FIG. 6, a grounded power supply plug 40 with cord 42 may be used as the connection for a source of power to be provided to the sterilization device 10. As will be understood by those skilled in the art, the cord 42 provides power to the ballast (not shown) which, in turn, provides a steady electrical current to the receptacles 30. Power is transferred from the ballast through transfer cables 46 to transfer cables 50 of each of the receptacles 30. The free ends of cables 46 and 50 include quick connect/disconnect couplers 48 and 52, respectively.

The circuitry of the air sterilization device 10 includes a fuse 54 which can handle any over current loading. Additionally, a safety shut-off switch 56 is provided to shut-off current flowing the receptacles 30 when the lid 15 is open. Switch 56 is in a normally open position when the lid is opened. When the lid is closed, switch trigger 58 causes the switch 56 to close thus allowing current to flow to the receptacles 30.

As shown in FIG. 6, when it is desired to mount the air sterilization device 10 to the duct 11, two openings 62 are drilled in the duct wall of a size which may receive the germicidal lamps 20. The housing 12 is mounted to the duct by a plurality of sheet metal screws 66 which are threadably received in screw holes 64 in the side wall of duct 11.

Referring back to FIG. 3, it can be seen that dust or other particulate matter is prevented from entering the housing 12 because the mounts 16 are flush against the duct wall and the holes 62 are sized to not exceed the diameter of the receptacles 30.

The housing 12 may be constructed of galvanized metal which is resilient to oxidation from exposure to moisture or other corrosive elements. An appropriate ballast for providing the desired current to the lamps is a 120 volt, 0.3 amp rapid start ballast. Additionally, a 2 amp fuse may be used which will prevent damage to most germicidal lamps. One recommended type of germicidal lamp that may be used in this invention is manufactured by Phillips, Model TUV PL-L (18 watt) long life germicidal lamp.

Although the preferred embodiment illustrates two germicidal lamps introduced within a duct, it shall be understood that the housing of this invention may be modified to include more or less lamps depending upon the needed ultraviolet saturization to sterilize a particular air flow. Additionally, it shall be understood that the germicidal lamps may be oriented within the air stream at a desired angle or position which best saturates the air flowing through that particular portion of the air handling unit. In some circumstances, it may be most effective to place the lamps in a transverse position as shown in FIG. 3. However, in other circumstances it may be desirable to reorient the lamps so they extend in a more parallel manner with respect to the direction of air flow.

By the foregoing, it is apparent that a simple structure is provided to enable the placement of germicidal lamps within an air duct. Because of the unitary construction of combining the receptacle 30 with the standard germicidal lamps 20, the germicidal lamps are much more capable of withstanding the high velocity and pressures associated with air flowing through an air handling unit. Accordingly, the lamps will remain in a rigid position within the air stream without damage occurring to either the lamps or to their mounts 16 within the housing. If it is necessary to replace or clean the lamps, the quick connects/disconnects are disconnected, and the receptacles are simply unscrewed from their mounts 16. If the germicidal lamp is burned out, it is replaced by another unit including a lamp and receptacle combination. Dust and other particulate matter which may normally clog sterilization devices used in air handling units is drastically reduced by sealing the lamps to their receptacles by means of a resin and by placing the mounts flush against the duct wall. Additionally, the threaded connection between the receptacles 30 and their corresponding mounts further reduces any migration of dust or other particulate matter into the housing 12.

I claim:

1. An ultraviolet air sterilization device for mounting in an air duct which carries a volume of moving air, said device comprising:

a housing;

a conduit mounting attached to said housing;

a receptacle removably mounted to said conduit mounting;

a lamp fixedly mounted to said receptacle so that said lamp is placed within the air duct and is exposed to the volume of moving air, said lamp including a lamp base;

a resin material placed in said receptacle and surrounding said lamp base to fixedly mount said lamp in said receptacle;

a first electrical connector communicating with said lamp base and mounted to said receptacle; and means for providing electrical power to said lamp, said power means including a second electrical connector removably connected to said first connector.

2. A device, as claimed in claim 1, further comprising:

a lid mounted to said housing for providing access to an interior of said housing; and a shut-off switch attached to said lid for controlling electrical power to said lamp base when said lid is opened.

3. A device, as claimed in claim 1, wherein:

said conduit mounting includes a plurality of inner threads, and said receptacle includes a plurality of outer threads for engagement with said plurality of inner threads to mount said receptacle to said conduit mounting.

4. A device, as claimed in claim 1, wherein:

said lamp is placed transversely to the direction of moving air.

5. A device, as claimed in claim 1, further including:

means for removably mounting said receptacle in said conduit mounting.

6. A device, as claimed in claim 1, wherein said housing includes:

a rear panel mounted against the air duct, said conduit mounting attached to said rear panel; and wherein an opening is formed in the air duct in alignment with said conduit mounting enabling said lamp to be inserted through the opening and within the air duct.

7. A device, as claimed in claim 1, wherein:

said lamp is sealed with respect to the air duct preventing dust and other particulate matter from entering said housing through the air duct.

8. An ultraviolet air sterilization device for mounting in an air duct which carries a volume of moving air, said device comprising:

a housing;

a lamp including a lamp base;

means for fixedly receiving said lamp including a resin material surrounding said lamp base;

means for removably mounting said lamp receiving means attached to said housing;

means for providing electrical power to said lamp base, said electrical providing means including a quick connect/disconnect enabling said lamp receiving means to be electrically separated from or connected to said removable mounting means.

9. A device, as claimed in claim 8, further comprising:

a lid mounted to said housing for providing access to an interior of said housing; and a shut-off switch attached to said lid for controlling electrical power to said lamp base when said lid is open.

10. A device, as claimed in claim 8, wherein:

said lamp is placed transversely to the direction of moving air.

11. A device, as claimed in claim 8, wherein:

said electrical providing means includes a ballast mounted in said housing and said quick connect/disconnect includes a first electrical connector communicating with said lamp base and mounted to said lamp receiving means, and a second electrical connector communicating with said ballast and removably connected to said first electrical connector.

12. A device, as claimed in claim 8, wherein said housing includes:

a rear panel mounted against the air duct, said removable mounting means attached to said rear panel; and wherein an opening is formed in the air duct in alignment with said removable mounting means enabling said lamp to be inserted through the opening and within the air duct.

13. A device, as claimed in claim 8, wherein:

said lamp is sealed with respect to the air duct preventing dust and other particulate matter from entering said housing through the air duct.

14. An ultraviolet air sterilization device which sanitizes a volume of air moving through an air duct in which the device includes a housing and a means for introducing an ultraviolet lamp into the volume of moving air, the improvement comprising:

a conduit mounting attached to said housing, said conduit mounting aligned with an opening formed in the air duct;

a receptacle removably mounted to said conduit mounting, the lamp being fixedly mounted to said receptacle so that the lamp is placed within the air duct and is exposed to the volume of moving air; and a resin material placed in said receptacle and surrounding said lamp to fixedly mount said lamp in said receptacle and thus stabilizing the lamp in the volume of moving air, and wherein the lamp is sealed with respect to the opening formed in the air duct so that migration of dust and other particulate matter is prevented from entering the housing.

15. A device, as claimed in claim 14, further including:

means for removably mounting said receptacle in said conduit mounting.

16. A device, as claimed in claim 14, wherein:

said lamp is placed transversely to the direction of moving air.

* * * * *